US006792946B1

United States Patent
Waldo, Jr. et al.

(10) Patent No.: US 6,792,946 B1
(45) Date of Patent: Sep. 21, 2004

(54) HEAT-MOISTURE EXCHANGER WITH AEROSOL BY-PASS

(76) Inventors: James V. Waldo, Jr., 3205 Grenada Way, Tampa, FL (US) 33618-3005; Christopher D. Warner, 2440 Walnut Heights Rd., Apopka, FL (US) 32703

(*) Notice: Subject to any disclaimer, the term of this patent is extended or adjusted under 35 U.S.C. 154(b) by 0 days.

(21) Appl. No.: 10/639,975

(22) Filed: Aug. 13, 2003

(51) Int. Cl.$^7$ .................................................. A62B 7/10
(52) U.S. Cl. ........................... 128/205.12; 128/201.13; 128/204.17
(58) Field of Search ............... 128/201.13, 203.16, 128/203.17, 203.26, 203.27, 204.17, 205.12, 911; 165/89, 90, 283, 297

(56) References Cited

U.S. PATENT DOCUMENTS

| | | | | |
|---|---|---|---|---|
| 3,802,495 A | * | 4/1974 | Hordis ......................... 165/89 |
| 4,007,737 A | * | 2/1977 | Paluch .................. 128/201.13 |
| 4,048,993 A | * | 9/1977 | Dobritz ................. 128/201.13 |
| 4,318,398 A | * | 3/1982 | Oetjen et al. .......... 128/201.13 |
| 4,327,717 A | * | 5/1982 | Oetjen et al. .......... 128/201.13 |
| 4,621,632 A | * | 11/1986 | Bartels et al. ......... 128/203.27 |
| 5,208,955 A | * | 5/1993 | Schiel ......................... 492/12 |
| 5,255,674 A | * | 10/1993 | Oftedal et al. ......... 128/203.16 |
| 5,435,298 A | * | 7/1995 | Anthony ................ 128/201.13 |
| 5,525,308 A | * | 6/1996 | Oser ........................... 422/171 |
| 6,017,374 A | * | 1/2000 | Huxham ..................... 55/315.2 |
| 6,095,135 A | * | 8/2000 | Clawson et al. ....... 128/201.13 |
| 6,105,576 A | * | 8/2000 | Clawson et al. ....... 128/205.12 |
| 6,415,788 B1 | * | 7/2002 | Clawson et al. ....... 128/201.13 |
| 6,474,335 B1 | * | 11/2002 | Lammers ............... 128/205.12 |
| 6,516,798 B1 | * | 2/2003 | Davies .................. 128/201.13 |
| 6,550,476 B1 | * | 4/2003 | Ryder .................... 128/201.13 |
| 6,564,799 B2 | * | 5/2003 | Fukunaga et al. ..... 128/205.29 |
| 6,588,421 B1 | * | 7/2003 | Diehl et al. ............ 128/201.13 |
| 6,745,766 B2 | * | 6/2004 | Fini ....................... 128/204.17 |

* cited by examiner

Primary Examiner—Aaron J. Lewis
(74) Attorney, Agent, or Firm—Larson & Larson, PA; James E. Larson

(57) ABSTRACT

A first and second housing joined together and rotatable with respect to each other, each housing having a conduit integral with an exterior wall, the conduits each having passageways leading to an internal portion of the respective housings. An internal edge of each housing mounts a heat-moisture exchange material having a transverse opening axially aligned with the passageway of the closest conduit. The passageway in the respective conduits are offset permitting passage of air to and from the patient through the heat-moisture material. The housings are rotated with respect to each other to axially align the passageways in the two conduits to permit passage of aerosol medicine through the exchanger without passing through the heat-moisture material.

20 Claims, 5 Drawing Sheets

HEAT-MOISTURE EXCHANGER WITH AEROSOL BY-PASS

FIELD OF ART

This invention relates to a patient heat-moisture exchanger attached to a nebulizer circuit. More particularly, it refers to a heat-moisture exchanger attached to a patient ventilator circuit, which includes a metered dose inhaler, the exchanger permitting medicament to pass through the heat moisture exchanger without passing through internally mounted filters and without disconnection from the ventilator circuit.

BACKGROUND OF THE INVENTION

A heat-moisture exchanger attached to a nebulization device is described in U.S. Pat. No. 6,550,476. This device has a rotatable second housing connected to a first housing. The first housing has at least two chambers enclosing an absorbent material and providing a passageway for an aerosol. The second housing encloses the nebulizer. Valves control the primary gas flow through a passageway to bypass the absorbent material. This device maintains the continuity of a closed ventilator circuit when administering an aerosolized medication to prevent interruption of ventilation to a patient. However, the device is complex and expensive to produce. A simpler device is needed to maintain the continuity of a closed ventilator circuit when administering an aerosolized medication to a patient connected to a ventilation system.

SUMMARY OF THE INVENTION

The present invention is directed towards a simplified way of maintaining the continuity of a closed ventilator circuit when administering an aerosolized medication to a patient. The inventive device has two annular housings rotatable with respect to each other. Each housing has a heat-moisture exchange material attached along an interior surface edge. Each heat moisture exchanger material (HMEM) has an annular opening axially aligned with an annular opening in the housing to which it is attached. A threaded tube is slidable through the openings in the two housings and the HMEM when the two housings are turned to a proper position, thereby allowing passage of an aerosol medication through the circuit. When the openings in the two housings and the HMEM are not aligned then the patient ventilator circuit is set for use as a conduit of air to and from the patient.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE BEST MODE

Figure 1:
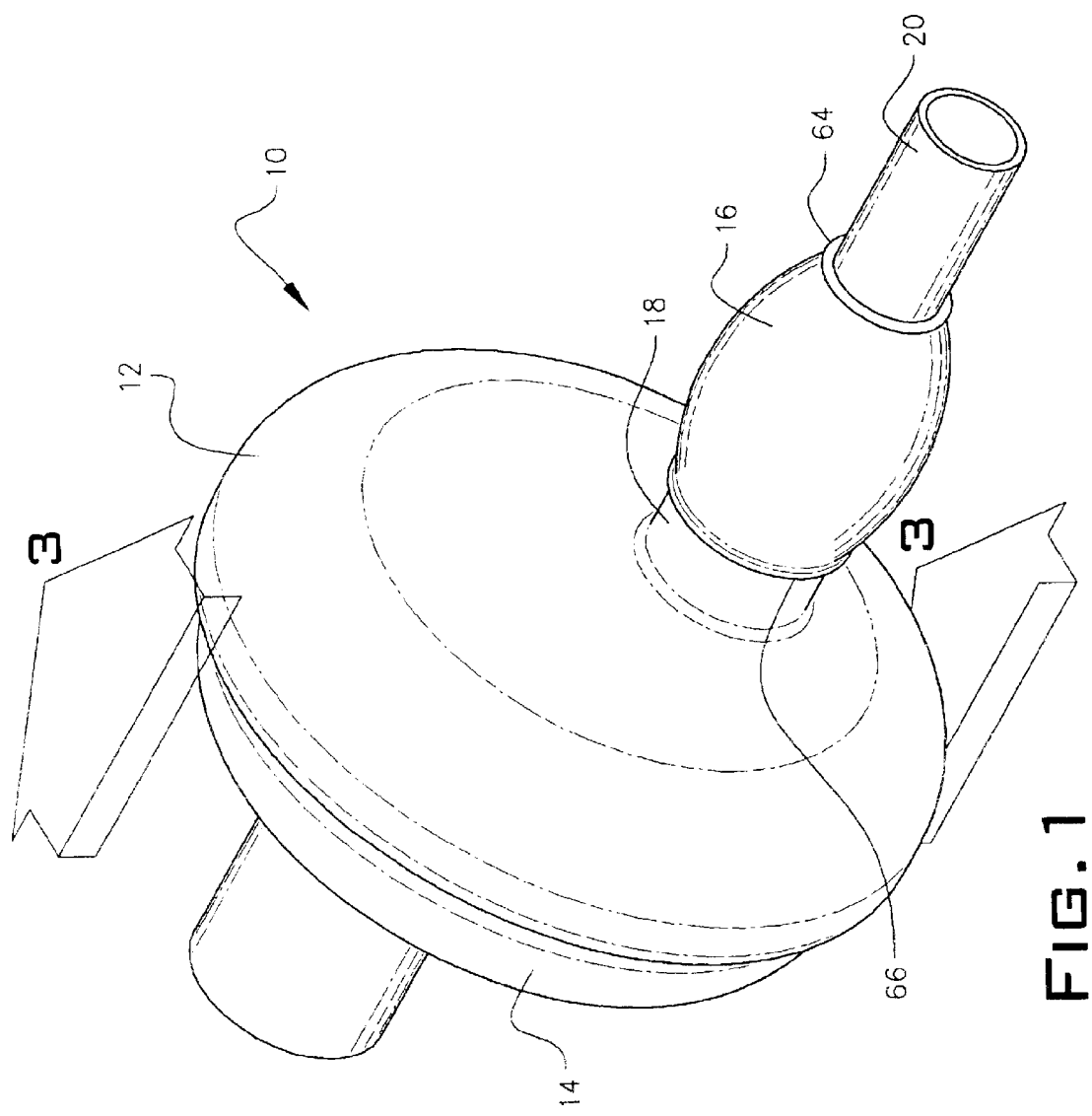
FIG. 1 is a perspective view of the heat-moisture exchanger of this invention.

Throughout the following detailed description, the same reference numerals refer to the same elements in all figures.

Referring to FIG. 1, the heat-moisture exchanger of this invention 10, has a first annular housing 12 and a second annular housing 14, rotatable with respect to each other. A protective cover 16 encloses the connection between a first conduit 18 integral with first annular housing 12 and a tubular member 20 slidable within first conduit 18.

Figure 2:
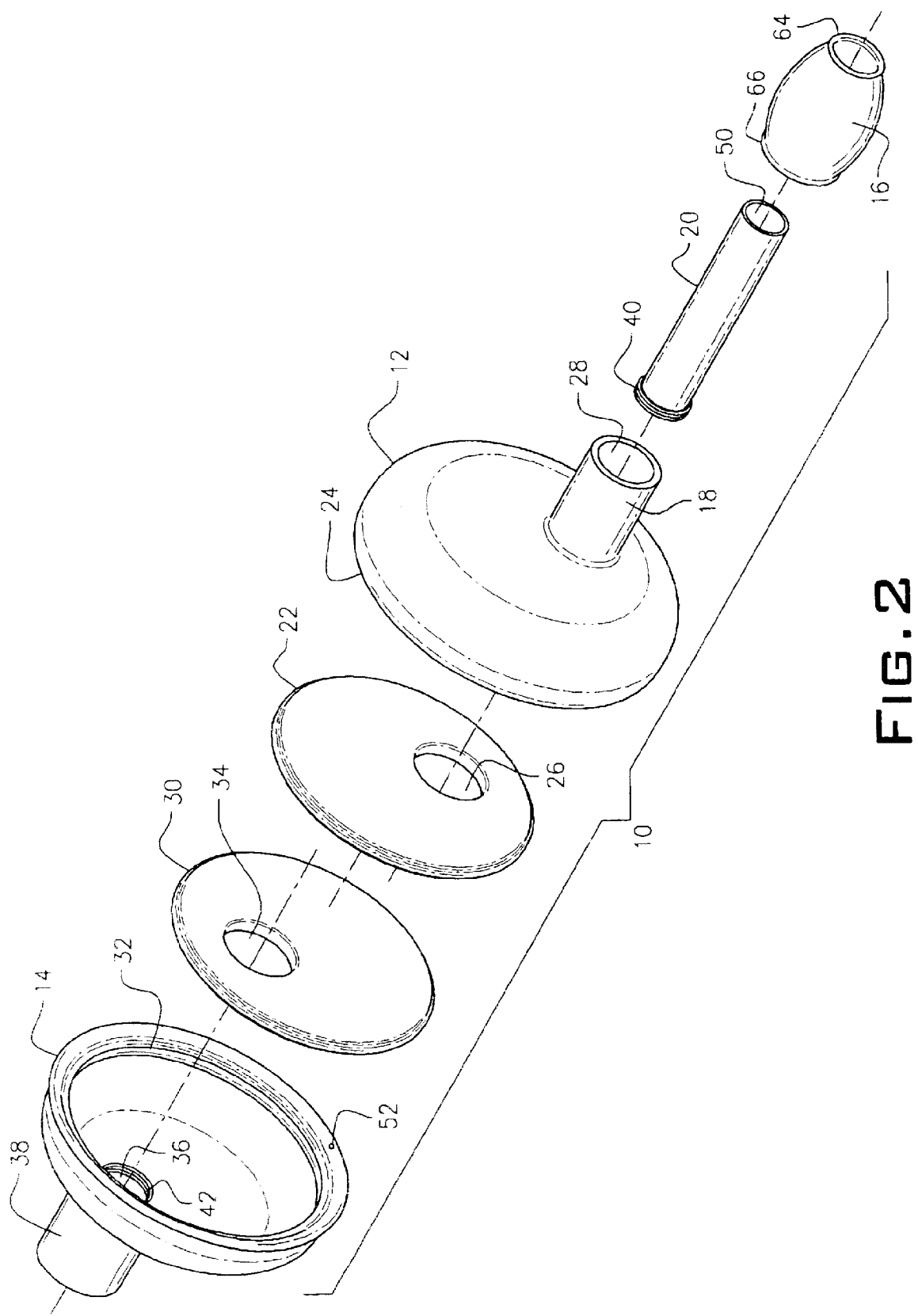
FIG. 2 is an exploded view showing the components of the heat-moisture exchanger of FIG. 1.

Referring to FIG. 2, a heat-moisture exchanger material 22 such as polyurethane foam coated in a sodium chloride solution is affixed to an inside edge 24 of first housing 12. The material 22 is affixed by gluing or other attaching methods. The material 22 has an annular opening 26 axially aligned with opening 28 in conduit 18. In like manner, heat-moisture exchanger material 30 is affixed to an inside edge 32 of the second annular housing 14. The material 30 has an annular opening 34 axially aligned with opening 36 in second conduit 38. Tube 20 has threads 40 on a distal end inserted through openings 28, 26, 34 and threadably engaging threads 42 in opening 36 when aerosolized medicine is being passed from a nebulizer 44 in an atomized flow towards the patient input 46. See FIG. 5.

Figure 3:
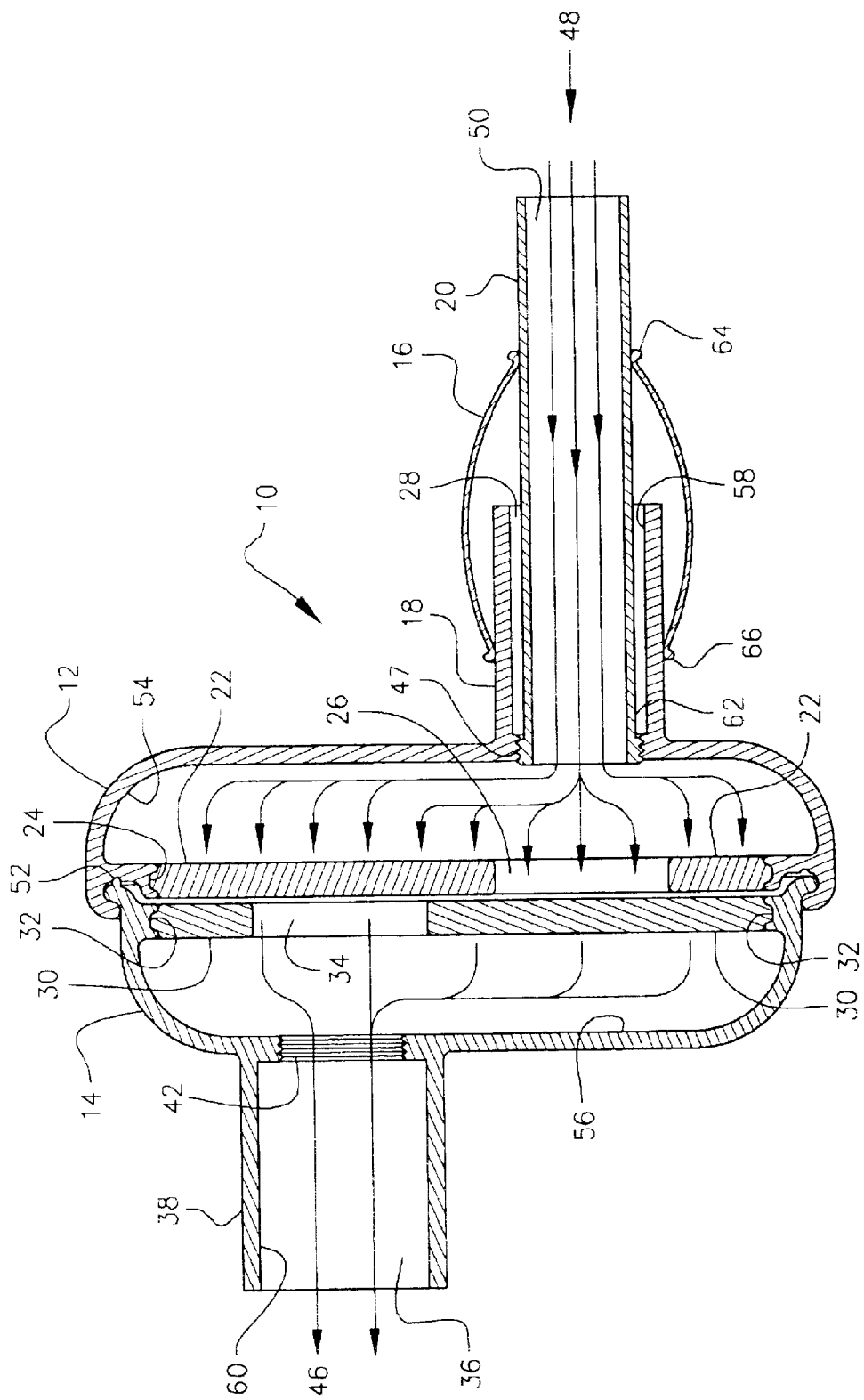
FIG. 3 is a cross-sectional view along lines 3—3 of FIG. 1 with the internal heat-moisture material filtering the flow of air.

Referring to FIG. 3, there is shown a typical heat-moisture ventilation circuit 48 wherein air enters tube 20 through proximal opening 50. In this condition, tube 20 is threaded to threads 47 in the first housing 12 and the axially aligned openings 28 and 26 are not aligned with axially aligned openings 36 and 34. Air to or from the patient 46 passes through the heat-moisture exchange material 22 and 30 in a typical ventilation circuit 48. The tube 20 and protective cover 16 can be connected on to either the first or second conduit and the patient air tube or air source can be connected to either the first or second conduit integral respectively with the first or second housing.

Figure 4:
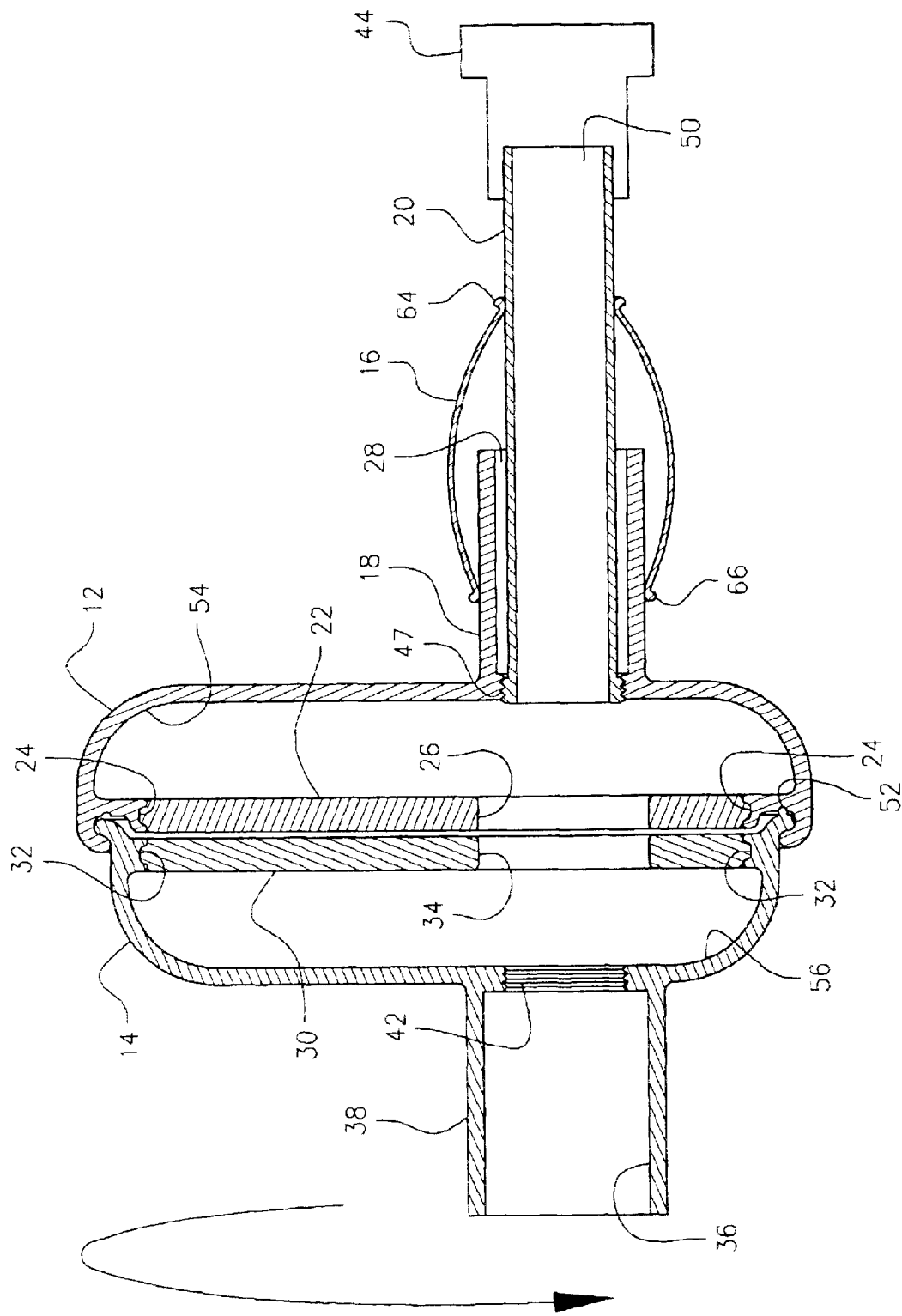
FIG. 4 is a cross-sectional view along line 3—3 of FIG. 1 with the bypass open prior to transmission of a medication from a metered patient dose inhaler.
Figure 5:
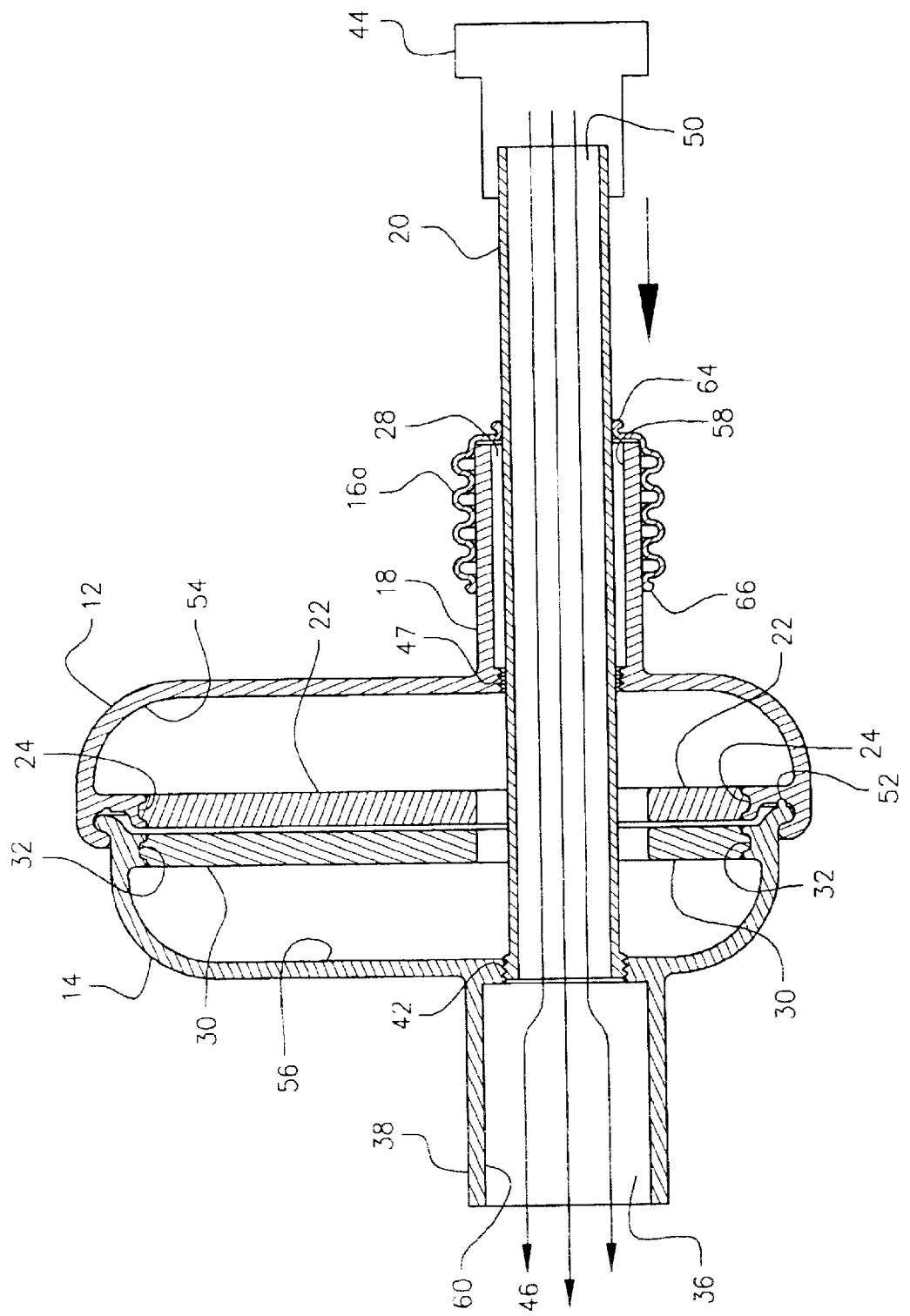
FIG. 5 is a cross-sectional view showing the medication flowing through the inventive device.

Referring to FIG. 4, the housings 12 and 16 can be turned with respect to each other to lock stop 52 so that openings 50, 28, 26, 34 and 36 are all axially aligned. In this condition, aerosolized medicine flows directly from nebulizer 44 through the openings to the patient 46. As seen in FIG. 5, the tube 20, slideable in passageway 58, has a distal end 62 unthreaded by turning past threads 47 and rethreaded at threads 42 at the opening to passageway 60 of conduit 38. As tube 20 is inserted to the opening to passageway 60, the protective cover 16 collapses, 16a, to seal the opening 28 of conduit 18. The protective cover 16 is glued to tube 20 and conduit 18 or attached by ultrasound.

The HMEM 22 mounted to the edge 24 of housing 12 is spaced from interior wall 54 of housing 12. In like manner HMEM 30 mounted to the edge 32 of housing 14 is spaced from interior wall 56 of housing 14.

The components shown above except for cover 16 and heat-moisture exchange material 30 and 32 are made from a rigid high strength plastic such as polypropylene, polyethylene, polyamide or polycarbonate. The HMEM is obtained from polyurethane foam coated in a sodium chloride solution. The protective cover 16 can be a pliable plastic such as polyethyleneterephthalate or an elastomeric material. The elastic ends 64 and 66 in protective cover 16 have an inside diameter slightly less than the outside diameter of tube 20 or conduit 18 so that cover 16 fits tightly over tube 20 and conduit 18.

By attaching the heat-moisture exchanger 10 of this invention to a patient ventilation system, the normal continuity of the exchanger circuit is not interrupted, but the modified circuit allows for entry of an aerosolized liquid medication from a nebulizer merely by turning the housings 12 and 14 to axially align all the openings. In this mode, the absorbent HME material is by-passed. The device 10 maintains the continuity of a closed ventilator circuit without interruption of the ventilation circuit to a patient.

Other substantially equivalent elements can be substituted for the elements of the heat-moisture exchanger disclosed herein to produce substantially the same results in substantially the same way.

Having disclosed the invention what is claimed follows:

1. A patient heat-moisture exchanger circuit in combination with an aerosol generator, comprising:

a first housing having a first conduit integral with an exterior side, the first conduit having a passageway leading inwardly through the exterior side of the first housing;

a heat-moisture exchange material affixed on an interior edge portion of the first housing, the heat-moisture exchange material having an opening therethrough axially aligned with the passageway in the first conduit;

a second housing joined to the first housing and rotatable with respect to the first housing, the second housing having a second conduit integral with an exterior side, the second conduit having a passageway leading inwardly through the exterior side of the second housing;

a heat-moisture exchange material affixed on an interior edge portion of the second hocusing, the heat-moisture exchange material having an opening therethrough axially aligned with the passageway in the second conduit;

an elongated tube slidably mounted within the passageway of the first conduit, with a protective cover over an entrance into the passageway of the first conduit, the elongated tube adapted to slide through the first housing and the heat-moisture materials affixed to the first and second housings when an atomized liquid is emanating from the aerosol generator and the first and second housings are turned with respect to each other so that the first and second conduits are axially aligned; and the elongated tube having a distal end abutting an entrance to the first housing when the first and second conduits are axially misaligned so that inspired and expired breath of the patient passes through the heat-moisture material.

2. The patient heat-moisture exchanger circuit according to claim 1 wherein the aerosol generator is a nebulizer.

3. The patient heat-moisture exchanger circuit according to claim 1 wherein the first and second conduits contain annular passageways having a diameter substantially the same as the diameter of the openings through the heat-moisture exchange materials.

4. The patient heat-moisture exchanger circuit according to claim 1 wherein an interior wall of the first and second housing is spaced apart from the heat-moisture exchange material.

5. The patient heat-moisture exchanger circuit according to claim 1 wherein the first and second housing with integral conduits and the elongated tube are rigid structures made from a high strength polymer.

6. The patient heat-moisture exchanger circuit according to claim 1 wherein the protective cover is an elongated flexible polymeric material glued at each end to the first conduit and elongated tube, respectively.

7. The patient heat-moisture exchanger circuit according to claim 1 wherein a stop tab on the first and second housing is engaged when the first and second conduits are axially aligned.

8. A system for alternatively passing a patient's expired breath through a heat-moisture exchange material and an axially aligned passageway to permit passage of an aerosolized medicament from an aerosol generator, the system comprising:

a first housing having a first conduit integral with an exterior surface, the conduit having an internal passageway leading through the exterior surface to an interior surface of the first housing;

a heat-moisture exchange material affixed around an interior edge portion of the first housing, the heat-moisture exchange material having a transverse opening axially aligned with the internal passageway of the first conduit.

a second housing joined to the first housing and rotatable with respect to the first housing, the second housing having a second conduit integral with an exterior surface, the conduit having an internal passageway leading through the exterior surface to an interior surface of the second housing;

a heat-moisture exchange material affixed around an interior edge portion of the second housing, the heat-moisture exchange material having a transverse opening axially aligned with the internal passageway of the second conduit; and a tube slidably engaged within the internal passageway of the first conduit with a protective cover over an entrance into the internal passageway.

9. A system according to claim 8 wherein the aerosol generator is a nebulizer.

10. The system according to claim 8 wherein an interior wall of the first and second housing is spaced apart from the heat-moisture exchange material.

11. The system according to claim 8 wherein the protective cover is an elongated flexible polymeric material attached by ultrasound at each end to the tube and the first conduit, respectively.

12. The system according to claim 8 wherein the protective cover is glued to the tube at a first end and to the first conduit at a second end.

13. The system according to claim 8 wherein a stop tab on an interior edge of the first and second housing are juxtaposed when the first and second conduits are axially aligned.

14. The system according to claim 8 wherein a threaded end of the tube is engaged to threads at an opening to the first housing when the internal passageways in the first and second conduits are offset.

15. The system according to claim 8 wherein a threaded end of the tube is engaged to threads at an opening to the second conduit when the internal passageways in the first and second conduits are axially aligned.

16. A patient heat-moisture exchange apparatus adapted to be connected to a joint patient air exchange circuit and an aerosol generator, comprising:

a first housing having a first conduit integral with an exterior side leading inwardly through the exterior side and a heat-moisture exchange material affixed on a interior edge portion of the first housing the heat-moisture exchange material having an opening therethrough axially aligned with a passageway in the first conduit;

a second housing attached to the first housing and rotatable with respect to the first housing, the second housing having a second conduit integral with an exterior side leading inwardly through the exterior side and a heat-moisture exchange material affixed on an interior edge portion of the second housing, the heat-moisture exchange material having an opening therethrough axially aligned with a passageway in the second conduit;

a tube slidably mounted within the first conduit with a protective cover over an entrance into the first conduit; and an entrance to the first and second conduit distal from the first and second housing respectively adapted to be connected to the patient air exchange circuit or an aerosol generator.

17. The patient heat-moisture exchange apparatus according to claim 16 wherein the aerosol generator is a nebulizer.

18. The patient heat-moisture exchange apparatus according to claim 17 wherein the first conduit is connected to a nebulizer.

19. The patient heat-moisture exchange apparatus according to claim 16 wherein the tube is slidable to the first housing when a passageway in the first and second conduits are offset.

20. The patient heat-moisture exchange apparatus according to claim 16 wherein the tube is slidable to the second housing when a passageway in the first and second conduits are axially aligned.

* * * * *